United States Patent [19]

Revelle

[11] Patent Number: 5,360,421
[45] Date of Patent: Nov. 1, 1994

[54] ABSORBENT TEXTILE GARMENT WITH BICOMPONENT TEXTILE LINER

[76] Inventor: David W. Revelle, RR1, Box 98B, Chaumont, N.Y. 13622

[21] Appl. No.: 106,612

[22] Filed: Aug. 16, 1993

[51] Int. Cl.$^5$ .................. A61F 13/15; A61F 13/20
[52] U.S. Cl. ........................ 604/378; 604/358; 604/371; 604/384; 604/385.1
[58] Field of Search .............. 604/358, 365-366, 604/370-371, 378-385.1

[56] References Cited

U.S. PATENT DOCUMENTS

| | | | |
|---|---|---|---|
| 4,493,866 | 1/1985 | Kim | 604/384 |
| 4,516,975 | 5/1985 | Mitchell | 604/385.2 |
| 4,573,987 | 3/1986 | Lamb, Jr. | 604/378 |
| 4,704,117 | 11/1987 | Mitchell | 604/391 |
| 4,923,454 | 5/1990 | Seymour et al. | 604/371 |
| 4,961,736 | 10/1990 | McCloud | 604/398 |
| 4,978,345 | 12/1990 | Holliday et al. | 604/384 |
| 5,037,409 | 8/1991 | Chen et al. | 604/370 |
| 5,085,653 | 2/1992 | Levy | 604/365 |
| 5,217,782 | 6/1993 | Moretz et al. | 604/358 |
| 5,267,991 | 12/1993 | Gillies et al. | 604/378 |

Primary Examiner—Randall L. Green
Assistant Examiner—P. Zuttarelli
Attorney, Agent, or Firm—Richard J. Johnson

[57] ABSTRACT

A washable and reusable absorbent garment designed to be fitted about the waist and legs and covering the groin and anal areas of a wearer. The garment includes a number of superimposed layers of textile material sewn together along their edges. Elastic material may be sewn in the material around the leg openings and waist to improve the fit. A liner material covers the inner surface of the garment. The liner layer of the garment or that portion which is next to the wearer's skin is a knitted bicomponent textile comprised of a brushed polyester outer layer which is interknitted with a nylon block co-polymer inner layer. The materials function to transfer moisture in both vapor and liquid form from the polyester side to the nylon side where it is dispersed and made available to the garment's second or absorbent layer. The two specific materials in the liner adjacent the wearer's skin and absorbent material work together to maintain a high degree of comfort for the wearer even after it has been wetted. The structural and functional integrity of the garment is maintained after repeated washings.

7 Claims, 1 Drawing Sheet

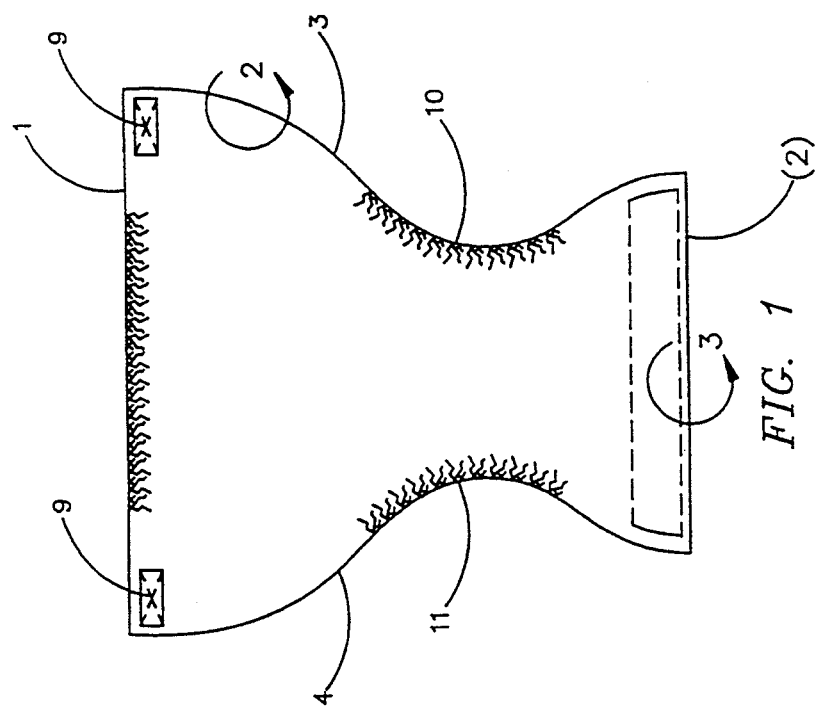
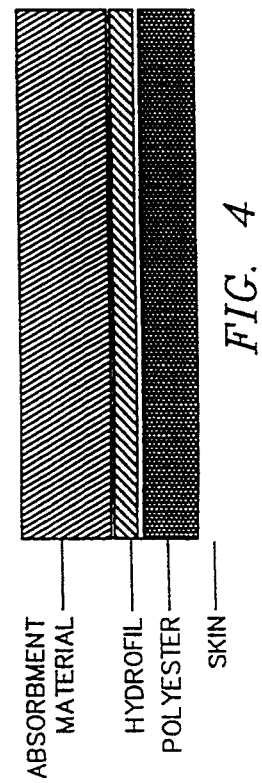
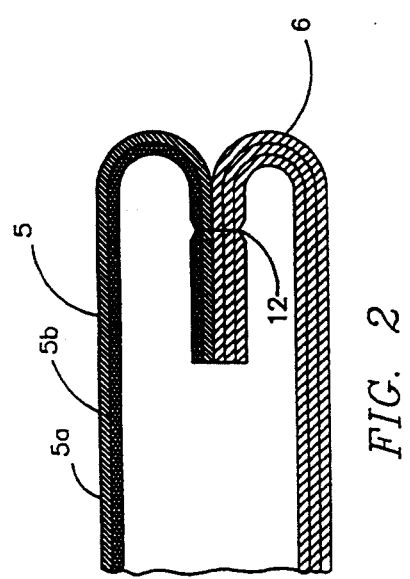
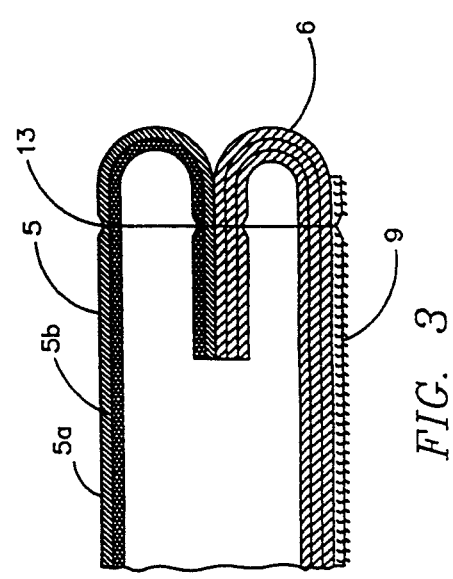

ABSORBENT TEXTILE GARMENT WITH BICOMPONENT TEXTILE LINER

BACKGROUND AND SUMMARY OF THE INVENTION

In one preferred embodiment, the present invention comprises a washable and reusable absorbent garment designed to be fitted about the waist and legs and covering the groin and anal areas of a wearer. The garment includes a number of superimposed layers of textile material sewn together along their edges. Elastic material may be sewn in the material around the leg openings and waist to improve the fit. A special liner material covers the inner surface of the garment.

A primary distinguishing feature of the invention over existing washable and reusable absorbent garments is in the use of the specific materials in the liner adjacent to and working in combination with the absorbent material to maintain a higher degree of comfort for the wearer and structural and functional integrity even after it has been repeatedly washed, than that of existing reusable absorbent garments.

The liner layer of the garment, or that portion which is next to the wearer's skin, is a knitted bicomponent textile comprised of a polyester outer layer which is interknitted with a nylon block co-polymer inner layer which functions to transfer moisture in both vapor and liquid form from the polyester side to the nylon side where it is dispersed and made available to the garment's second or absorbent layer. The nylon material is manufactured under the trademark Hydrofil by Allied Signal Inc. The knitted bicomponent material produced is sometimes referred to as a "Push/Pull" fabric in that the body pushes moisture from the skin through the polyester material and the Hydrofil nylon pulls it away. One product useful for the intended purpose is manufactured by Faytex Corporation and is sold under the name "DRILEX." The outer brushed polyester layer stays soft and dry to the skin even when the absorbent layer has become substantially saturated with moisture.

The second or absorbent layer is a highly absorbent body of several layers of textile material, such as woven cotton, which readily absorbs moisture from the nylon side of the liner layer.

The two layers work together in a synergistic-like manner in the unexpectedly efficient removal of wetness, particularly urine and sweat, from physical contact with the wearer's skin and at the same time retain the soft comfortable feel of a dry garment. The latter is of particular importance when used as a diaper wherein a wet garment against the skin is uncomfortable and can cause a variety of skin problems.

BRIEF DESCRIPTION OF THE DRAWINGS

FIG. 1 a top view of the garment laid flat and with the inside of the garment uppermost.

FIG. 2 is a sectional view of the side and back seams taken along the line 2—2 in FIG. 1.

FIG. 3 is a sectional view of the front seam 2 taken along the line 3—3 in FIG. 1.

FIG. 4 is an enlarged diagramatic view of the diaper in cross-section showing the arrangement of the layers of material.

DETAILED DESCRIPTION OF THE INVENTION

In one preferred embodiment, illustrated in FIG. 1, a conventional hourglass shaped diaper is shown. However, the invention is not limited to any specific shaped article or use. The first layer or liner 5 is comprised of a bicomponent knitted textile of brushed polyester 5a on one side and knitted nylon block co-polymer 5b on the other side. The polyester material which is hydrophobic and the nylon which is hydrophilic are interknitted at their central portions. The brushed polyester hydrophobic side 5a is positioned outwardly to engage the wearer's skin while the inner hydrophilic nylon side 5b is in engagement with and passes moisture to the garment's absorbent second layer 6. The nylon portion of the liner material is marketed under the brand name Hydrofil by Allied Signal Inc. Hydrofil nylon is a block copolymer of nylon 6 and polyethylene oxide diamine. One suitable liner material formed as a bicomponent woven fabric of Hydrofil nylon and polyester is marketed by the Faytex Corporation under the brand name "DRILEX."

The absorbent layer 6 may be composed of cotton, rayon, or other absorbent materials preferably arranged for example in superimposed layers. As illustrated in FIG. 2, the layers 6a, 6b, and 6c are of woven cotton fabric although a variety of other absorbent materials may be used as long as such will maintain their structural and functional integrity after repeated washings.

The bicomponent layer 5 is superimposed upon the absorbent body 6 with the nylon side facing the absorbent body. The layers are stitched together along both sides 3,4 and along the back edge 1. Elastic tape is inserted in the seams at the leg openings 10, 11 and in the middle section of the back edge 1 and stretched during stitching to provide elastic gathers at the leg openings and waist to improve the fit.

The garment is constructed by sewing along the edges of the two layers which are then turned inside-out such that the polyester side of the bicomponent layer 5 is facing out and the raw sewn edges of the material are inside the garment. The exposed and unstitched edges at the front edge 2 of the garment are then turned into the garment and topstitched at 13 as illustrated in FIG. 3. Hook and loop tape segments as illustrated at 7,8 are stitched to the side corners along the back edge 1, parallel to the back edge, and with their rear surfaces engaging the polyester side of the bicomponent layer 5. A corresponding segment of hook and loop tape 9 is secured to the absorbent body 6 along and generally parallel to the front edge of the garment with the reverse side of the tape contacting the absorbent body 6.

The nature of this invention is such that it could be applied to a variety of specific configurations. While the liner has been described as being coextensive with and sewn to the absorbent material, in some instances it could cover less than the full extent of the garment inner surface. For example, it could be omitted from the securing tabs and comprise a generally rectangular member. Also, it could be designed to be removable from the absorbent material such as by the use of hook and loop segments. The invention relates primarily to the new combination and arrangement of materials used in the repeatedly washable garment. It should be recognized that the shape of the garment and its details could be changed without affecting the function of the invention. Therefore, the specific configuration shown and described herein is for illustrative purposes only and is not meant to be restrictive.

What is claimed is:

1. A washable and reusable diaper type garment adapted to absorb and retain body fluids and adapted to maintain its structural and functional integrity after repeated washings and wherein said garment comprises: an absorbent body of textile material, a knitted textile liner overlying and adjacent to said absorbent material, with said liner and said absorbent body being substantially coextensive with and forming said garment substantially in its entirety, said liner comprising a bicomponent fabric layer constructed of nylon block copolymer and polyester interknitted together to provide a material layer having a nylon face and an opposite polyester face, said polyester face being brushed and positioned to engage a wearer's skin, said nylon face being positioned to permit moisture transfer from said polyester face to said absorbent material.

2. The garment of claim 1 wherein the liner covers less than the entire inner surface of the garment.

3. The garment of claim 1 wherein the liner is coextensive with one surface of the garment and is sewn thereto.

4. The garment of claim 3 wherein the absorbent body comprises multiple layers of woven textile material adapted to maintain their structural and functional integrity after repeated washings.

5. The garment of claim 4 wherein the absorbent material is comprised of rayon.

6. A washable and reusable diaper adapted to absorb and retain body fluids and adapted to maintain its structural and functional integrity after repeated washings, wherein said garment comprises: an absorbent body comprised of rayon textile material, a knitted textile liner overlying, coextensive with, and adjacent to said absorbent material, said liner comprising a bicomponent fabric layer constructed of nylon block co-polymer and polyester interknitted together to provide a material layer having a nylon face and an opposite polyester face, said polyester face being brushed and positioned to engage a wearer's skin, said nylon face being positioned to permit moisture transfer from said polyester face to said rayon absorbent material.

7. The diaper of claim 6 wherein the absorbent body comprises multiple layers of material.

* * * * *